(12) United States Patent
Smith et al.

(10) Patent No.: US 10,018,575 B2
(45) Date of Patent: Jul. 10, 2018

(54) INSPECTABLE BLACK GLASS CONTAINERS

(71) Applicant: Owens-Brockway Glass Container Inc., Perrysburg, OH (US)

(72) Inventors: Roger P. Smith, Perrysburg, OH (US); Carol A. Click, Corning, NY (US); Rebecca Mullen, Rolla, MO (US); Stephen Daniel Barton, Dansville, NY (US)

(73) Assignee: Owens-Brockway Glass Container Inc., Perrysburg, OH (US)

( * ) Notice: Subject to any disclaimer, the term of this patent is extended or adjusted under 35 U.S.C. 154(b) by 0 days.

(21) Appl. No.: 15/019,405

(22) Filed: Feb. 9, 2016

(65) Prior Publication Data

US 2016/0153919 A1    Jun. 2, 2016

Related U.S. Application Data

(62) Division of application No. 13/666,644, filed on Nov. 1, 2012, now Pat. No. 9,296,641.

(51) Int. Cl.
*G01N 21/90* (2006.01)
*G01N 33/38* (2006.01)
(Continued)

(52) U.S. Cl.
CPC .......... *G01N 21/958* (2013.01); *C03B 32/00* (2013.01); *C03C 3/087* (2013.01); *C03C 4/02* (2013.01);
(Continued)

(58) Field of Classification Search
CPC ......... G01N 33/386; G01N 2021/8845; G01N 21/35; G01N 21/8806; G01N 21/3563;
(Continued)

(56) References Cited

U.S. PATENT DOCUMENTS

| 1,242,336 A | 10/1917 | Fitts | |
|---|---|---|---|
| 1,899,230 A * | 2/1933 | Crowell | C03C 1/04 106/312 |

(Continued)

FOREIGN PATENT DOCUMENTS

| GB | 636151 | 4/1950 | |
|---|---|---|---|
| JP | 2006027930 A * | 2/2006 | C03C 4/02 |

OTHER PUBLICATIONS

Lindsey, Bill Bottle colors page as viewed at https://sha.org/bottle/colors.htm on Aug. 29, 2017 copyright Apr. 22, 2007.*

(Continued)

*Primary Examiner* — Jodi C Franklin

(57) ABSTRACT

A soda-lime-silica glass container and related methods of manufacturing. A black-strikable glass composition having a base glass portion and a latent colorant portion is prepared. The base glass portion includes soda-lime-silica glass materials and one or more blue colorant materials, and the latent colorant portion includes cuprous oxide ($Cu_2O$), stannous oxide (SnO), bismuth oxide ($Bi_2O_3$), and carbon (C). Glass containers may be formed from the black-strikable glass composition, and these glass containers may be heated to a temperature greater than 600 degrees Celsius to strike black therein. The glass containers formed from the black-strikable glass composition may be inspected—before or after striking—by infrared inspection equipment.

15 Claims, 2 Drawing Sheets

(51) Int. Cl.
*C03C 4/02* (2006.01)
*C03B 32/00* (2006.01)
*G01N 21/958* (2006.01)
*G01J 5/28* (2006.01)
*C03C 3/087* (2006.01)
*G01N 21/88* (2006.01)

(52) U.S. Cl.
CPC ............ *G01J 5/28* (2013.01); *G01N 21/8806* (2013.01); *G01N 21/909* (2013.01); *G01N 33/386* (2013.01); *G01N 2021/8845* (2013.01); *Y10T 428/131* (2015.01)

(58) Field of Classification Search
CPC .... G01N 21/359; G01N 21/909; G01N 21/95; G01N 21/88; G01N 21/8803; C03C 4/02
USPC ...................... 65/158, 29.12, 29.11, 160, 377
See application file for complete search history.

(56) References Cited

U.S. PATENT DOCUMENTS

| | | | |
|---|---|---|---|
| 2,174,554 A | 10/1939 | Dobrovolny et al. | |
| 2,233,343 A | 2/1941 | Dobrovolny et al. | |
| 2,309,071 A * | 1/1943 | Sullivan | C03C 1/10 501/27 |
| 2,353,354 A * | 7/1944 | Nordberg | C03C 4/02 172/122 |
| 2,473,958 A | 6/1949 | Kreidl | |
| 2,524,719 A | 10/1950 | Tillyer | |
| 2,672,423 A | 3/1954 | Lobdell et al. | |
| 2,776,900 A | 1/1957 | Duncan et al. | |
| 2,902,377 A | 9/1959 | Duncan et al. | |
| 2,922,720 A | 1/1960 | Parks | |
| 2,976,161 A | 3/1961 | Smith | |
| 3,300,289 A | 1/1967 | Long | |
| 3,345,190 A | 10/1967 | Albinak et al. | |
| 3,361,550 A | 1/1968 | Murphy et al. | |
| 3,498,806 A | 3/1970 | Hammer et al. | |
| 3,513,003 A | 5/1970 | Hammer et al. | |
| 3,607,170 A | 9/1971 | Malesak | |
| 3,627,548 A | 12/1971 | Hammer et al. | |
| 3,951,633 A | 4/1976 | Danihel | |
| 3,982,918 A | 9/1976 | Frieser et al. | |
| 4,059,389 A * | 11/1977 | Armstrong | F21K 5/02 431/362 |
| 4,127,689 A | 11/1978 | Holt | |
| 4,139,307 A * | 2/1979 | Clarke | G01N 21/8901 250/559.06 |
| 4,256,957 A * | 3/1981 | Ford | G01N 21/8851 209/524 |
| 4,312,953 A | 1/1982 | Mills et al. | |
| 4,323,423 A | 4/1982 | Schrunk | |
| 4,421,542 A * | 12/1983 | Poad | B07C 5/122 209/3.2 |
| 4,436,776 A | 3/1984 | Wojcik | |
| 4,619,850 A | 10/1986 | Charlton | |
| 4,692,799 A * | 9/1987 | Saitoh | G01N 21/94 226/45 |
| 4,740,401 A | 4/1988 | Barkhan et al. | |
| 5,059,561 A | 10/1991 | Ciolek et al. | |
| 5,144,151 A * | 9/1992 | Thorne | G01N 21/958 250/341.8 |
| 5,541,142 A | 7/1996 | Araujo | |
| 5,611,834 A * | 3/1997 | Walter | C03B 23/112 65/102 |
| 5,710,081 A * | 1/1998 | Tunker | C03C 8/02 296/84.1 |
| 5,864,395 A * | 1/1999 | Laurberg | G01N 21/9027 250/223 B |
| 6,067,155 A * | 5/2000 | Ringlien | G01N 21/90 250/208.1 |
| 6,099,905 A | 8/2000 | Roquette | |
| 6,100,209 A | 8/2000 | Bentem et al. | |
| 6,175,107 B1 * | 1/2001 | Juvinall | G01N 21/9054 250/223 B |
| 6,372,327 B1 | 4/2002 | Burnham et al. | |
| 6,753,527 B1 * | 6/2004 | Yamagishi | G01F 23/2921 250/223 B |
| 6,796,146 B2 | 9/2004 | Burnham | |
| 6,911,653 B2 * | 6/2005 | Yagita | G01N 15/0227 250/339.06 |
| 6,993,176 B2 * | 1/2006 | Yamagishi | G01F 23/292 250/223 B |
| 6,997,018 B2 | 2/2006 | Sakoske et al. | |
| 7,340,086 B2 * | 3/2008 | Werzinger | G01N 21/8851 209/524 |
| 7,612,003 B2 | 11/2009 | Lefevre et al. | |
| 7,659,221 B2 | 2/2010 | Arbab et al. | |
| 7,696,113 B2 * | 4/2010 | Ellison | C03C 3/091 501/66 |
| 7,821,629 B2 * | 10/2010 | Akkerman | G01N 21/9045 356/237.1 |
| 7,902,097 B2 | 3/2011 | Cid-Aguilar et al. | |
| 8,021,739 B2 | 9/2011 | Nedelec | |
| 8,196,807 B2 | 6/2012 | Grimard | |
| 8,245,538 B2 | 8/2012 | Kimura et al. | |
| 8,318,054 B2 * | 11/2012 | Cid-Aguilar | C03C 3/087 252/588 |
| 8,464,558 B2 | 6/2013 | Abensour et al. | |
| 2002/0033943 A1 * | 3/2002 | Clauberg | G01N 21/9081 356/240.1 |
| 2002/0102388 A1 | 8/2002 | Burnham | |
| 2002/0154809 A1 * | 10/2002 | Yamagishi | G01F 23/292 382/142 |
| 2003/0037569 A1 | 2/2003 | Arbab et al. | |
| 2004/0038799 A1 * | 2/2004 | Landa | C03C 1/00 501/70 |
| 2004/0071982 A1 * | 4/2004 | Seto | C03C 3/087 428/426 |
| 2004/0237590 A1 | 12/2004 | Sakoske et al. | |
| 2005/0061033 A1 | 3/2005 | Petrany et al. | |
| 2005/0211789 A1 | 9/2005 | Hsieh et al. | |
| 2005/0218126 A1 | 10/2005 | Leyvraz | |
| 2006/0008133 A1 * | 1/2006 | Dordoni | G01N 21/8851 382/142 |
| 2006/0059948 A1 * | 3/2006 | Sato | C03B 19/1453 65/32.1 |
| 2006/0066846 A1 * | 3/2006 | Chen | G01N 21/8851 356/239.1 |
| 2006/0211563 A1 * | 9/2006 | Arbab | C03C 3/087 501/70 |
| 2007/0054793 A1 * | 3/2007 | Sakoske | C03B 27/012 501/29 |
| 2007/0191208 A1 * | 8/2007 | Teyssedre | C03C 4/02 501/71 |
| 2008/0055348 A1 | 3/2008 | Deeter et al. | |
| 2008/0057266 A1 | 3/2008 | Johnson et al. | |
| 2008/0269038 A1 | 10/2008 | Schneider et al. | |
| 2008/0290082 A1 | 11/2008 | Tallet | |
| 2009/0098370 A1 * | 4/2009 | Sato | C03B 19/1453 428/333 |
| 2010/0101275 A1 | 4/2010 | Abensour et al. | |
| 2010/0107692 A1 | 5/2010 | Han | |
| 2010/0118912 A1 * | 5/2010 | Lai | G01N 25/72 374/5 |
| 2010/0255603 A9 | 10/2010 | Putnam et al. | |
| 2011/0071012 A1 * | 3/2011 | Kondo | C03C 3/085 501/71 |
| 2012/0216568 A1 * | 8/2012 | Fisher, Jr. | C03B 5/235 65/29.21 |
| 2013/0104980 A1 * | 5/2013 | Sridharan | B81C 1/00317 136/259 |
| 2013/0128434 A1 | 5/2013 | Yamamoto et al. | |
| 2013/0201678 A1 * | 8/2013 | Siebers | C03B 32/02 362/231 |
| 2014/0029108 A1 * | 1/2014 | Bockmeyer | G02B 5/205 359/642 |

(56) References Cited

U.S. PATENT DOCUMENTS

2014/0117240 A1     5/2014   Smith et al.
2014/0120278 A1     5/2014   Ordway et al.
2015/0037503 A1*   2/2015   Chisholm ............... B05C 13/02
                                                                            427/282

OTHER PUBLICATIONS

W. Simpson & D. D. Myers, The Redox Number Concept and its Use by the Glass Technologist, vol. 19, No. 4, Aug. 4, 1978, pp. 82-85, XP002718217.
PCT Search Report and Written Opinion, Int. Application No. PCT/US2013/063205, Int. Filing Date: Oct. 3, 2014, Applicant: Owens-Brockway Glass Container Inc., dated Mar. 26, 2014.

* cited by examiner

INSPECTABLE BLACK GLASS CONTAINERS

The present disclosure is directed to glass containers and, more particularly, to coloring of glass containers.

BACKGROUND AND SUMMARY OF THE DISCLOSURE

Glass containers are often composed of so-called soda-lime glass, also called soda-lime-silica glass. Many such containers are colored, for example, for aesthetic or functional purposes. Colored glass containers may be produced from soda-lime glass compositions which include one or more colorants. For example, blue glass containers can be made from soda-lime glass compositions which include cobalt oxide (CoO) as a colorant. U.S. Patents that illustrate colored glass compositions of this type include U.S. Pat. Nos. 3,326,702, 3,330,638, 3,345,190, 3,498,806, and 4,312,953.

Some colorants in soda-lime glass do not immediately impart color to the glass. Instead, color may need to be developed in the colorant-containing glass by a heat-treatment process known as "striking." In this process, glass containers are formed from a glass composition which contains "latent" colorants. Thereafter, the glass containers are heated to a temperature slightly above normal annealing temperatures so that the latent colorants in the glass interact or "strike" to impart color to the glass. U.S. Patents that illustrate this method of coloring glass containers include U.S. Pat. Nos. 2,672,423, 3,513,003, and/or 3,627,548.

A general object, in accordance with one aspect of the disclosure, is to provide a glass composition that may be used to produce cobalt blue glass containers that, upon heat treatment and striking, develop a visually black color. Accordingly, this glass composition and the glass containers formed therefrom may be referred to as "black-strikable." The glass containers may be inspected—before or after striking—by infrared inspection equipment in a glass container production line or in a container filling operation. Accordingly, these glass containers also may be referred to as "inspectable." Until now, the optical inspection of black glass containers had been thought impossible due to their low percentage of light transmission.

The present disclosure embodies a number of aspects that can be implemented separately from or in combination with each other.

In accordance with an aspect of the disclosure, there is provided a method of making a black-strikable glass container. In this method, a black-strikable glass composition is prepared having a base glass portion and a latent colorant portion. The base glass portion includes: 60-75 wt. % $SiO_2$, 7-15 wt. % $Na_2O$, 6-12 wt. % CaO, 0.1-3.0 wt. % $Al_2O_3$, 0.0-2.0 wt. % MgO, 0.0-2.0 wt. % $K_2O$, 0.01-0.25 wt. % $SO_3$, 0.01-0.25 wt. % $Fe_2O_3$, and 0.01-0.15 wt. % CoO. The latent colorant portion includes: 0.0875-0.35 wt. % cuprous oxide ($Cu_2O$), 0.06-0.5 wt. % stannous oxide (SnO), 0.006-0.05 wt. % bismuth oxide ($Bi_2O_3$), and 0.02-0.10 wt. % carbon (C). Thereafter, a black-strikable glass container is formed from the black-strikable glass composition.

In accordance with another aspect of the disclosure, there is provided a method of inspecting a black glass container for commercial variations that affect optical characteristics of the glass container. In this method, infrared light energy is directed onto and through the black glass container, and is received on an infrared light sensor. The infrared light sensor is responsive to infrared light energy received thereon having wavelengths in the range of 750-1100 nm.

BRIEF DESCRIPTION OF THE DRAWINGS

The disclosure, together with additional objects, features, advantages and aspects thereof, will be best understood from the following description, the appended claims and the accompanying drawings, in which:

DETAILED DESCRIPTION

Figure 1:
FIG. 1 is a side elevation of a glass container in accordance with an exemplary embodiment of the present disclosure.

FIG. 1 illustrates an exemplary embodiment of a glass container 10 (e.g., glass bottle, jar, or the like) that may be produced in accordance with an exemplary embodiment of a presently disclosed manufacturing process, as described further herein below. The glass container 10 may be referred to as "inspectable," meaning that the glass container 10 transmits a sufficient amount of infrared light to be inspected by infrared inspection equipment in a glass container production line or in a container filling operation.

The glass container 10 may be produced by the following method. Additional exemplary conditions and procedures for composing and melting production container glass can be found in, e.g. the Handbook of Glass Manufacture by Fay V. Tooley (3rd ed., Ashlee Publishing 1984).

The method may include preparing a black-strikable glass composition. The black-strikable glass composition may be thought of as having a base glass portion and a latent colorant portion.

The base glass portion may include soda-lime-silica glass materials and one or more blue colorant materials. For example, the base glass portion may include substantially the same materials present in cobalt blue glass.

The term "cobalt blue glass" is employed in its conventional sense in glass technology as referring to a glass having blue coloration (e.g., blue glass). A presently preferred cobalt blue glass may comprise the following materials in the following ranges of amounts by weight:

| | |
|---|---|
| 60-75% | $SiO_2$ |
| 7-15% | $Na_2O$ |
| 6-12% | CaO |
| 0.1-3.0% | $Al_2O_3$ |
| 0.0-2.0% | MgO |
| 0.0-2.0% | $K_2O$ |
| 0.01-0.25% | $SO_3$ |
| 0.01-0.25% | $Fe_2O_3$ |
| 0.01-0.15% | CoO. |

More particularly, and by way of example only, a presently preferred cobalt blue glass may comprise the following materials in substantially the stated amounts by weight:

| | |
|---|---|
| 73% | $SiO_2$ |
| 13% | $Na_2O$ |
| 11% | CaO |
| 1.6% | $Al_2O_3$ |
| 0.5% | MgO |
| 0.4% | $K_2O$ |
| 0.15% | $SO_3$ |

-continued

| 0.10% | $Fe_2O_3$ |
| 0.06% | CoO. |

The latent colorant portion of the black-strikable glass composition may include cuprous oxide ($Cu_2O$), stannous oxide (SnO), bismuth oxide ($Bi_2O_3$), and carbon (C), as this combination of materials has been found to enable the striking of copper (Cu) in soda-lime glass containers.

The molar ratio of tin oxide (SnO) to copper oxide ($Cu_2O$) in the latent colorant portion may be about one, for example, the molar ratio may be in the range of 0.9 to 1, or in the range of about 1 to 0.9. However, the latent colorant portion suitably may contain an excess of tin oxide (SnO). For example, when an excess of tin oxide (SnO) is present in the latent colorant portion, the molar ratio of tin oxide (SnO) to copper oxide ($Cu_2O$) may be about 1.5.

In one embodiment, the black-strikable glass composition may include about 0.175 wt. % cuprous oxide ($Cu_2O$), about 0.25 wt. % stannous oxide (SnO), about 0.0125 wt. % bismuth oxide ($Bi_2O_3$), and about 0.06 wt. % carbon (C). For example, the black-strikable glass composition may include 0.0875-0.35 wt. % cuprous oxide ($Cu_2O$), 0.06-0.5 wt. % stannous oxide (SnO), 0.006-0.05 wt. % bismuth oxide ($Bi_2O_3$), and 0.02-0.10 wt. % carbon (C). In another embodiment, the black-strikable glass composition may include substantially 0.175 wt. % cuprous oxide ($Cu_2O$), substantially 0.25 wt. % stannous oxide (SnO), substantially 0.0125 wt. % bismuth oxide ($Bi_2O_3$), and substantially 0.06 wt. % carbon (C). As used herein the term "substantially" means within manufacturing tolerances customary in the glass container manufacturing industry.

The remaining portion of black-strikable glass composition may include small amounts of other materials. Such materials may be additives, residual materials from cullet, and/or impurities typical in the glass container manufacturing industry. Such materials may be present in trace amounts, for example, less than 0.2 wt. %. In one specific example, the remaining portion of the black-strikable glass composition may include trace amounts of $TiO_2$, BaO, and/or SrO.

The method also may include forming black-strikable glass containers from the black-strikable glass composition. A feeder located at a downstream end of the one or more forehearths may be used to measure out gobs of molten glass and to deliver them to glass container-forming machines. Thereafter, the gobs may be formed into glass containers, for example, by press-and-blow or blow-and-blow processes and by individual section machines, or in any other suitable manner by any suitable equipment.

The method further may include annealing the black-strikable glass containers in any suitable manner, for example, in an annealing lehr. At an entry, hot end, or upstream portion of the annealing lehr, the temperature therein may be between 550 and 600 degrees Celsius. Through the lehr, the temperature may be brought down gradually to a downstream portion, cool end, or exit of the lehr, for example, to a temperature therein of between 130 degrees Celsius and 65 degrees Celsius. In any event, the glass containers may be annealed, preferably between 550 and 600 degrees Celsius for 30 to 90 minutes, more preferably between 525 and 575 degrees Celsius for 45 to 75 minutes, and most preferably at substantially 550 degrees Celsius for one hour.

The method also may include raising the temperature of the black-strikable glass containers above the highest temperature at which they are annealed (i.e., the highest annealing temperature) to strike black coloration into the glass containers. Accordingly, this temperature-raising step may be referred to as "striking."

The striking or temperature-raising step may include, for example, heat-treating the glass containers between 600 and 680 degrees Celsius for 10 to 90 minutes to produce black glass containers. In a more specific example, the temperature-raising step may include heat-treating the black-strikable glass containers between 630 and 650 degrees Celsius for 30 to 40 minutes.

In one embodiment, the temperature raising or striking step may be carried out after the annealing step. For example, a furnace or secondary lehr may be used in line or off line downstream of the annealing lehr. The temperature of the glass containers may be raised in the furnace or secondary lehr to a temperature and for a time suitable to strike black into the glass containers. Thereafter, the temperature of the black glass containers may be brought down gradually, for example, according to an annealing schedule to avoid fracture or failure of the containers.

In another embodiment, the temperature raising or striking step may be carried out between the time the annealing step begins and the time the annealing step ends. In one example, a separate furnace may be used off line adjacent to the annealing lehr. In another example, the annealing lehr may be operated in accordance with a modified heating profile. For instance, the modified heating profile may include a typical annealing temperature profile modified to include temperatures and times suitable to strike black into the glass containers before, during, or after annealing.

The black-strikable glass containers may, in some respects, have a container glass composition that is different from the black-strikable glass composition. For example, the amount of sulfur trioxide ($SO_3$) retained in the glass containers may be substantially less than the amount of sulfur trioxide ($SO_3$) in the black-strikable glass composition. The actual amount of sulfur trioxide ($SO_3$) retained in the glass containers will vary depending on the amount of carbon (C) in the black-strikable glass composition. In suitable embodiments, the amount of sulfur trioxide ($SO_3$) retained in the glass containers will be in the range of 0.01 to 0.22 wt. %. In general, the more carbon (C) in the black-strikable glass composition, the less sulfur trioxide ($SO_3$) will be retained in the glass containers. As another example, the latent colorant materials of $Cu_2O$, SnO, and $Bi_2O_3$ may be largely retained in the container glass composition. For example, about 75-100% of the $Cu_2O$, SnO, and $Bi_2O_3$ in the black-strikable glass composition may be retained in the container glass composition.

A struck-black glass container produced in accordance with this disclosure may have a wall thickness of greater than 0.040 inches (i.e., greater than about 1 mm). At this wall thickness, the glass container transmits a minimal amount of light at wavelengths between 390 nm and 700 nm and, thus, appears visually black to the human eye in natural lighting conditions (e.g., indirect sunlight) at arm's length. For example, a struck-black glass container produced in accordance with this disclosure may transmit light in an amount less than 10% at wavelengths between 390 nm and 675 nm.

At the same time, a struck-black glass container produced in accordance with this disclosure transmits infrared light in the near-infrared region of the electromagnetic spectrum (e.g., from about 750 nm to 1100 nm) and, thus, may be inspected by infrared inspection equipment in a glass container production line or in a container filling operation. For example, a struck-black glass container produced in accordance with this disclosure may transmit light in an amount between about 30% and about 65% at wavelengths between 750 nm and 850 nm. In one specific example, a struck-black glass container produced in accordance with this disclosure may transmit light in an amount of at least 40% at a wavelength of 750 nm.

Glass containers produced in accordance with this disclosure may be inspected—either before or after striking—to detect for commercial variations in the glass. Such commercial variations may include, for example, dimensional anomalies in the sidewalls, heels, bottoms, shoulders, and/or necks of the glass containers, as well as inhomogeneities in the glass itself that affect the optical properties of the glass containers. Some of these commercial variations may be within commercially acceptable standards or thresholds, while other variations may be outside of such standards or thresholds, and thus may be unacceptable.

A suitable apparatus for detection of commercial variations in a glass container produced in accordance with this disclosure includes a light source, a light receiver, and an information processor. The light source may include a lamp or a laser capable of emitting infrared light in the near-infrared region of the electromagnetic spectrum (e.g., from about 750 nm to 1100 nm), and the light receiver may include a laser optic sensor responsive to light energy at wavelengths in the range of about 750 nm to 1100 nm.

A glass container produced in accordance with this disclosure may be inspected by directing light energy from an infrared light source through the glass container and onto a light sensor. In one embodiment, infrared light in the near-infrared region of the electromagnetic spectrum may be directed through the glass container and onto the light sensor. In another embodiment, infrared light at wavelengths in the range of about 750-850 nm may be directed through the glass container and onto the light sensor. In response, the light sensor may provide electrical signals to an information processor, which may analyze the electrical signals to determine whether the glass container is commercially acceptable or unacceptable. Before the present discovery, no known commercially available black glass containers were believed to be capable of inspection using an infrared light source.

According to the present disclosure, a black-strikable glass composition is provided that may be used to produce cobalt blue glass containers and optionally black glass containers by the process of "striking." In addition, the glass containers produced according to the present disclosure may be inspected—before or after striking—by infrared inspection equipment in a glass container production line or in a container filling operation.

Several glass test samples were prepared in a laboratory environment and color was observed in each sample.

EXAMPLE 1

In the following example, a batch of raw materials was prepared and used to produce 300 g of molten glass. The batch of raw materials included the necessary raw materials to produce a black-strikable glass composition. The necessary amount of each raw material for the batch was weighted out in accordance with standard batch calculation practice common in the glass industry. Thereafter, the raw materials were crushed and ground using a mortar and pestle to break up agglomerate material, and then mixed together using a mixer for about ten minutes. While mixing, a crucible was pre-heated in a furnace at 1350 degrees Celsius for about ten minutes. The crucible was removed from the furnace and the entire batch of raw materials was added to the crucible. The crucible was again placed in the furnace, and the temperature of the furnace was increased to form a glass melt having a temperature of about 1450 degrees Celsius. The glass melt was held at that temperature for about 3.5 hours.

Thereafter, the molten glass was poured into splat quenched patties. Some of the patties were placed in an annealing oven at 550 degrees Celsius, and some of the patties were left unannealed. The patties which were placed in the annealing oven were annealed at a temperature of about 550 degrees Celsius for about 10 to 20 minutes, and then a door of the annealing oven was cracked open until the annealing oven temperature decreased to a temperature of about 300 degrees Celsius. Thereafter, the annealing oven temperature was set to 20 degrees Celsius to let the glass cool down to room temperature overnight.

After the black-strikable glass patties were annealed, they were heat treated at oven temperatures of 550, 600, and 650 degrees Celsius for durations of 15 to 90 minutes. At 600 and 650 degrees Celsius, the samples struck black by 30 minutes.

Figure 2:
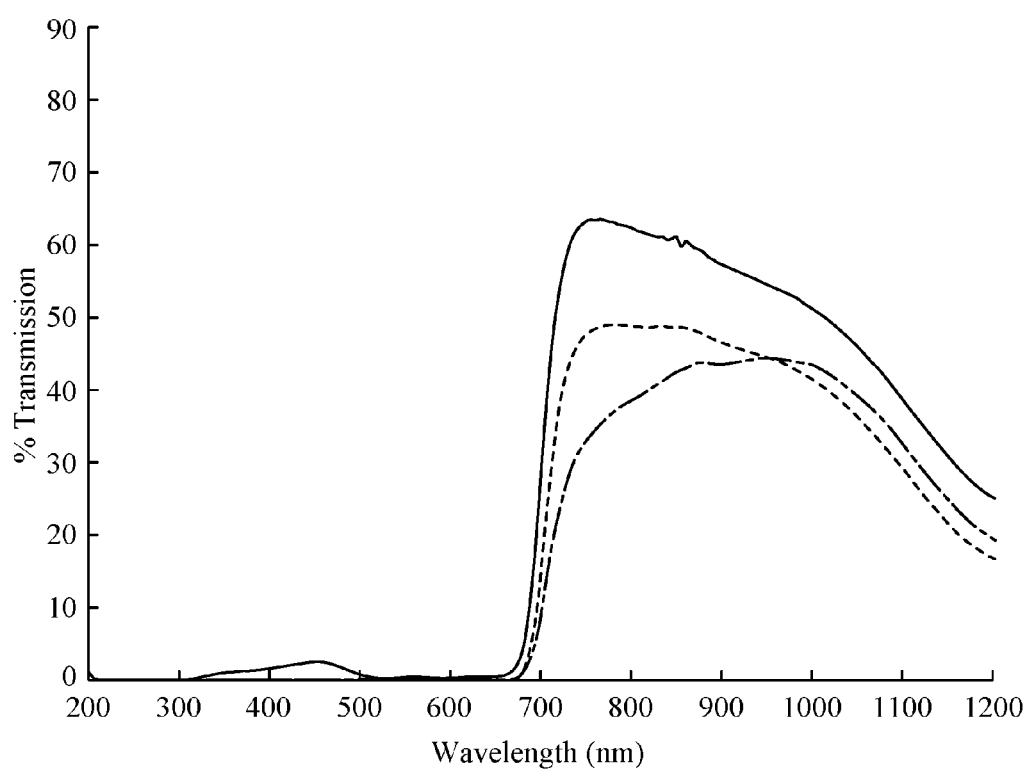
FIG. 2 is a graphical plot of light transmission through samples of inspectable struck-black container glass doped with three different amounts of copper oxide ($Cu_2O$).

FIG. 2 illustrates three plots of Transmission (%) vs. Wavelength (nm) through samples of cobalt blue glass doped with suitable amounts of the disclosed latent colorant materials. However, each of the samples was doped with a different amount of copper oxide ($Cu_2O$). The three plots illustrate samples doped with 0.12 wt. % $Cu_2O$ (dash dot), 0.15 wt. % $Cu_2O$ (dashed), and 0.175 wt. % $Cu_2O$ (solid), respectively. As shown, these struck-black samples exhibit 0% to 5% transmission at wavelengths between 200 nm and 390 nm (ultraviolet light), 0% to 10% transmission at wavelengths between 390 nm and 675 nm (visible light), and 30% to 65% transmission at wavelengths between 750 nm and 850 nm (infrared light). Therefore, a struck-black glass container formed by doping a cobalt blue glass with suitable amounts of the disclosed latent colorant materials transmits a sufficient amount of infrared light so as to be inspected by infrared inspection equipment.

There thus has been disclosed suitable methods of producing a black-strikable glass composition and black-strikable glass containers that fully satisfy all of the objects and aims previously set forth. The disclosure has been presented in conjunction with several exemplary embodiments, and additional modifications and variations have been discussed. Other modifications and variations readily will suggest themselves to persons of ordinary skill in the art in view of the foregoing discussion. The disclosure is intended to embrace all such modifications and variations as fall within the spirit and broad scope of the appended claims.

The invention claimed is:

1. A method of inspecting a black glass container for commercial variations that affect optical characteristics of the glass container, the method including the steps of:

providing a black glass container having a transmittance of less than 10% to all visible light energy having wavelengths between 390 nm and 675 nm and having a transmittance of greater than 30% to infrared light energy having wavelengths between 750 nm and 1100 nm so as to be inspectable using infrared light energy, the black glass container having a composition that includes a base glass portion and a latent colorant portion, with the base glass portion including: 60-75 wt. % $SiO_2$, 7-15 wt. % $Na_2O$, 6-12 wt. % CaO, 0.1-3.0 wt. % $Al_2O_3$, 0.0-2.0 wt. % MgO, 0.0-2.0 wt. % $K_2O$, 0.01-0.25 wt. % $SO_3$, 0.01-0.25 wt. % $Fe_2O_3$, and 0.01-0.15 wt. % CoO and the latent colorant portion including: 0.0875-0.35 wt. % cuprous oxide ($Cu_2O$), 0.06-0.5 wt. % stannous oxide (SnO), and 0.006-0.05 wt. % bismuth oxide ($Bi_2O_3$);

directing infrared light energy onto the black glass container; and receiving infrared light energy from the black glass container on an infrared light sensor, the infrared light sensor being responsive to infrared light energy having wavelengths in the range of 750 nm to 1100 nm.

2. The method as set forth in claim 1 wherein the infrared light sensor is a laser optic sensor and is responsive to infrared light energy having wavelengths in the range of 750 nm to 850 nm.

3. The method set forth in claim 1 including the additional steps of:

providing electrical signals from the infrared light sensor to an information processor in response to infrared light energy received from the black glass container; and analyzing the electrical signals at the information processor to determine whether commercial variations in the black glass container are acceptable or unacceptable.

4. The method as set forth in claim 1 wherein the black glass container has a transmittance in the range of 30% to 65% to infrared light energy having wavelengths in the range of 750 nm to 850 nm.

5. The method as set forth in claim 1 wherein the black glass container has a transmittance of greater than 30% to light having wavelengths between 750 nm and 850 nm.

6. The method as set forth in claim 1 wherein the black glass container has a transmittance of at least 40% to light having a wavelength of 750 nm.

7. The method as set forth in claim 1 wherein the black glass container has a wall thickness of greater than one millimeter.

8. The method set forth in claim 3 including:

analyzing the electrical signals at the information processor to detect for dimensional anomalies in a sidewall, heel, bottom, shoulder, or neck of the glass container.

9. A method of making black glass containers including:

preparing a molten black-strikable glass composition, the black-strikable glass composition having a base glass portion and a latent colorant portion, with the base glass portion comprising: 60-75 wt. % $SiO_2$, 7-15 wt. % $Na_2O$, 6-12 wt. % CaO, 0.1-3.0 wt. % $Al_2O_3$, 0.0-2.0 wt. % MgO, 0.0-2.0 wt. % $K_2O$, 0.01-0.25 wt. % $SO_3$, 0.01-0.25 wt. % $Fe_2O_3$, and 0.01-0.15 wt. % CoO, and the latent colorant portion comprising: 0.0875-0.35 wt. % cuprous oxide ($Cu_2O$), 0.06-0.5 wt. % stannous oxide (SnO), 0.006-0.05 wt. % bismuth oxide ($Bi_2O_3$), and 0.02-0.10 wt. % carbon (C);

forming glass containers from the molten black-strikable glass composition;

raising the temperature of the glass containers above 600 degrees Celsius to strike black coloration into the glass containers to produce black glass containers having a transmittance of less than 10% to all visible light energy having wavelengths in the range of 390 nm to 675 nm and a transmittance of greater than 30% to infrared light energy having wavelengths in the range of 750 nm to 1100 nm so as to be inspectable using infrared light energy; and inspecting the black glass containers by directing infrared light energy from an infrared light source through the black glass containers and onto an infrared light sensor, the infrared light sensor being responsive to infrared light energy having wavelengths in the range of 750 nm to 1100 nm.

10. The method set forth in claim 9 including:

transmitting electrical signals from the infrared light sensor to an information processor in response to infrared light energy received by the infrared light source; and analyzing the electrical signals at the information processor to detect for commercial variations that affect optical characteristics of the black glass containers.

11. The method set forth in claim 9 wherein the glass containers are formed from the molten black-strikable glass composition by measuring out gobs of the molten black-strikable glass composition and delivering the gobs to glass container-forming machines.

12. An inspectable black glass container comprising:

a base glass portion comprising 60-75 wt. % $SiO_2$, 7-15 wt. % $Na_2O$, 6-12 wt. % CaO, 0.1-3.0 wt. % $Al_2O_3$, 0.0-2.0 wt. % MgO, 0.0-2.0 wt. % $K_2O$, 0.01-0.25 wt. % $SO_3$, 0.01-0.25 wt. % $Fe_2O_3$, and 0.01-0.15 wt. % CoO; and a latent colorant portion comprising: 0.0875-0.35 wt. % cuprous oxide ($Cu_2O$), 0.06-0.5 wt. % stannous oxide (SnO), 0.006-0.05 wt. % bismuth oxide ($Bi_2O_3$), and 0.02-0.10 wt. % carbon (C), wherein the black glass container has a transmittance of less than 10% to all visible light energy having wavelengths between 390 nm and 675 nm, and wherein the black glass container transmits 30% to 65% infrared light so as to be inspectable using an infrared light source.

13. The glass container set forth in claim 12 wherein the black glass container has a transmittance of greater than 30% to light having wavelengths between 750 nm and 850 nm.

14. The glass container set forth in claim 12 wherein the black glass container has a transmittance of at least 40% to light having a wavelength of 750 nm.

15. The glass container set forth in claim 1 wherein the black glass container has a transmittance of greater than 30% to all infrared light energy having wavelengths between 750 nm and 1100 nm.

* * * * *